US008183019B2

(12) United States Patent
Lenz et al.

(10) Patent No.: US 8,183,019 B2
(45) Date of Patent: May 22, 2012

(54) METHOD FOR PREPARING 3-HYDROXY-4-HYDROXYMETHYL-PYRROLIDINE COMPOUNDS

(75) Inventors: Dirk Henning Lenz, Wellington (NZ);
Jennifer Mary Mason, Wellington (NZ); Keith Clinch, Wellington (NZ);
Gary Brian Evans, Wellington (NZ);
Peter Charles Tyler, Wellington (NZ)

(73) Assignee: Industrial Research Limited, Lower Hutt (NZ)

( * ) Notice: Subject to any disclaimer, the term of this patent is extended or adjusted under 35 U.S.C. 154(b) by 1028 days.

(21) Appl. No.: 11/628,427

(22) PCT Filed: Jun. 3, 2005

(86) PCT No.: PCT/NZ2005/000114
§ 371 (c)(1),
(2), (4) Date: Mar. 26, 2008

(87) PCT Pub. No.: WO2005/118532
PCT Pub. Date: Dec. 15, 2005

(65) Prior Publication Data
US 2008/0280334 A1 Nov. 13, 2008

(30) Foreign Application Priority Data
Jun. 4, 2004 (NZ) .................................. 533360

(51) Int. Cl.
*C12P 17/10* (2006.01)
*C07D 295/00* (2006.01)
(52) U.S. Cl. ........ 435/121; 435/117; 435/195; 435/197; 435/198; 435/196; 548/531
(58) Field of Classification Search .................. 435/117, 435/121, 195, 196, 197, 198; 548/531
See application file for complete search history.

(56) References Cited

U.S. PATENT DOCUMENTS

| | | | |
|---|---|---|---|
| 5,985,848 A | 11/1999 | Furneaux et al. | |
| 6,066,722 A | 5/2000 | Furneaux et al. | |
| 6,228,847 B1 | 5/2001 | Furneaux et al. | |
| 6,239,163 B1 | 5/2001 | Jessen et al. | |
| 6,379,911 B2 | 4/2002 | Schramm et al. | |
| 6,458,799 B1 | 10/2002 | Montgomery et al. | |
| 6,492,347 B2 | 12/2002 | Furneaux et al. | |
| 6,693,193 B1 | 2/2004 | Furneaux et al. | |
| 6,764,829 B2 | 7/2004 | Schramm et al. | |
| 6,803,455 B2 | 10/2004 | Furneaux et al. | |
| 7,022,852 B2 | 4/2006 | Furneaux et al. | |
| 7,098,334 B2 | 8/2006 | Furneaux et al. | |
| 7,109,331 B2 | 9/2006 | Furneaux et al. | |
| 7,153,851 B2 | 12/2006 | Asahina et al. | |
| 7,211,653 B2 | 5/2007 | Furneaux et al. | |
| 7,211,677 B2 | 5/2007 | Furneaux et al. | |
| 7,390,890 B2 | 6/2008 | Furneaux et al. | |
| 7,405,297 B2 | 7/2008 | Furneaux et al. | |
| 7,553,839 B2 | 6/2009 | Evans et al. | |
| 7,655,795 B2 | 2/2010 | Evans et al. | |
| 2006/0160765 A1 | 7/2006 | Evans et al. | |
| 2006/0217551 A1 | 9/2006 | Evans et al. | |
| 2007/0161634 A1 | 7/2007 | Pei et al. | |
| 2009/0233948 A1 | 9/2009 | Evans et al. | |
| 2009/0239885 A1 | 9/2009 | Evans et al. | |
| 2009/0325986 A1 | 12/2009 | Furneaux et al. | |
| 2010/0062995 A1 | 3/2010 | Schramm | |
| 2010/0094003 A1 | 4/2010 | Evans et al. | |
| 2010/0168141 A1 | 7/2010 | Evans et al. | |
| 2010/0222370 A1 | 9/2010 | Schramm et al. | |
| 2011/0046167 A1 | 2/2011 | Clinch et al. | |
| 2011/0086812 A1 | 4/2011 | Schramm | |
| 2011/0092521 A1 | 4/2011 | Furneaux et al. | |
| 2011/0130412 A1 | 6/2011 | Clinch et al. | |
| 2011/0190265 A1 | 8/2011 | Schramm | |

FOREIGN PATENT DOCUMENTS

| | | | |
|---|---|---|---|
| JP | 9003043 A | | 1/1997 |
| WO | 00/55132 A1 | | 9/2000 |
| WO | WO 2004018496 A1 | * | 3/2004 |
| WO | 200503307 A1 | | 4/2005 |
| WO | WO 2006/014913 A2 | | 2/2006 |
| WO | WO 2006/123953 A1 | | 11/2006 |
| WO | 2007016291 A2 | | 2/2007 |
| WO | WO 2007/069923 A1 | | 6/2007 |
| WO | WO 2007/097647 A1 | | 8/2007 |
| WO | WO 2007/097648 A1 | | 8/2007 |
| WO | 2008030119 A1 | | 3/2008 |
| WO | 2009082247 A1 | | 7/2009 |
| WO | 2010033236 A2 | | 2/2010 |
| WO | 2011008110 A1 | | 1/2011 |

OTHER PUBLICATIONS

STN File CA abstract No. 91-123648 (4 pages), (1979) downloaded Jan. 4, 2006.
Galeazzi, R et al., "Chiral 3-hydroxypyrrolidin-2-ones from a Baylis-Hillman adduct: convergent, stereoselective synthesis of a glycosidase inhibitor," Tertrahedron: Asymmetry, 2004 vol. 15 pp. 3249-3256.
Kametani, T et al., "Studies on the Syntheses of Heterocylic Compounds. 762. Synthesis of 3-benzyl-6-methyl-2-oxo-3,6-diazabicyclo[3.1.0]hexane as a synthetic intermediate of mitomycins," Tetrahedron, 1979, 35(3), pp. 313-316.
Banker G S et al., entitled "Modern Pharmaceutics," Marcel Dekker Inc., Third Edition, Revised and Expanded, 1996, pp. 451 & 596.
"Biocryst Pharmaceuticals, Inc. Announces Preliminary Phase II Trial Data for a Topical Ointment formulation of PNP Drug Drug Candidate, BCX-34" Biocryst News, Apr. 29, 1998.
Brakta M et al, entitled "Efficient Synthesis of 3H,5H-Pyrrolo[3,2-d] pyrimidin-4-one," J. Chem. Soc. Perkin Trans., 1992, vol. 1, pp. 1883-1884.

(Continued)

*Primary Examiner* — Susan Hanley
(74) *Attorney, Agent, or Firm* — Amster, Rothstein & Ebenstein LLP

(57) ABSTRACT

A process is disclosed for preparing (3R,4R)-3-hydroxy-4-hydroxymethylpyrrolidine, the compound of formula (I), or (3S,4S)-3-hydroxy-4-hydroxymethylpyrrolidine, the compound of formula (Ia) involving, as a key step, the enzyme-catalysed enantioselective hydrolysis of a racemic 3,4-trans-disubstituted pyrrolidinone compound of formula (II).

37 Claims, No Drawings

OTHER PUBLICATIONS

Evans G B et al., entitled "Exploring structure-activity relationships of transition state analogues of human purine nucleoside phosphorylase," J. Med. Chem. 2003, 46, 3412-3423.

Evans G B et al. "Synthesis of a transition state analogue inhibitor of purine nucleoside phosphorylase via the Mannich reaction," Organic Letters 2003, 5(20), 3639-3640.

Filichev V V et al., entitled "Synthesis of 1'-aza-C-nucleosides from (3R,4R)-4-(hydroxymethyl)pyrrolidin-3-ol," Tetrahedron 57 (2001) 9163-9168.

Kamath V P et al., entitled "Synthesis of a potent transition-state inhibitor of 5'-Deoxy-5'-methylthioadenosine phosphorylase," J. Med. Chem. 2004, 47, 1322-1324.

Karlsson S et al., entitled "Synthesis of enantiomerically pure 4-substituted pyrrolidin-3-ols via asymmetric 1,3-dipolar cycloaddition," Tetrahedron: Asymmetry 12 (2001) 1977-1982.

Lewandowicz A et al., entitled "Over-the barrier transition state analoques and crystal structure with Mycobacterium tubersulosis purine nucleoside phosphorylase," Biochemistry 2003, 42, 6057-6066.

Lewandowicz A et al. "Energetic Mapping of Transition State Analogue Internations with Human and Plasmodium falciparum Purine Nucleotide Phosphorylases" Journal of Biological Chemistry, 2005, 280(34), 30320-30328.

Lim M-I et al., entitled "A New Synthesis of Pyrrolo[3,2-d]pyrimidines ("9-Deazapurines") via 3-Amino-2-carboalkoxypyrroles," J. Org. Chem., 1979, vol. 44, No. 22, pp. 3826-3829.

Supplementary European Search Report for European Application No. EP 05 75 7531.8, 3 pages, dated Jul. 16, 2007.

Wolff M E, entitled "Burger's Medicinal Chemistry and Drug Discovery," Fifth Edition, vol. 1: Principles and Practice, John Wiley & Sons, 1995, 975-977.

Miles R W et al., entitled "One-Third-the-Sites Transition-State Inhibitors for Purine Nucleoside Phosphorylase," Biochemistry, 1998, vol. 37, No. 24, pp. 6-12.

Taylor E C et al., entitled "An Expeditious Synthesis of 2-Amino-4(3H)-oxo-5H-pyrrolo[3,2-d] pyrimidine (9-Deazaguanine)," Tetrahedron Letters, 1993, vol. 34, No. 29, pp. 4595-4598.

Evans G B et al., entitled "Synthesis of second-generation transition state analogues of human purine nucleoside phosphorylase," J Med Chem 46:5271-6, 2003.

Dill J, "Relative Tetrahedral Stereochemistry" Jan. 9, 2002, downloaded from http://www.cambridgesoft.com/services/documentation/sdk/chemfinder/Features/Features701/Rel_Stereo/index.htm on Nov. 2, 2011, 6 pages.

* cited by examiner

METHOD FOR PREPARING 3-HYDROXY-4-HYDROXYMETHYL-PYRROLIDINE COMPOUNDS

CROSS-REFERENCE TO RELATED APPLICATIONS

This application is a national stage entry under 35 U.S.C. §371 of PCT International Application No. PCT/NZ2005/000114, filed Jun. 3, 2005, and claims priority of New Zealand Application No. 533360, filed Jun. 4, 2004, the contents of which are incorporated herein by reference in their entirety.

TECHNICAL FIELD

This invention relates to a method for preparing 3-hydroxy-4-hydroxymethylpyrrolidine compounds. In particular, the invention relates to a method for preparing (3R,4R)-3-hydroxy-4-hydroxymethylpyrrolidine or its enantiomer (3S,4S)-3-hydroxy-4-hydroxymethylpyrrolidine. The invention further relates to the preparation of purine nucleoside phosphorylase (PNP) inhibitors from the above compounds.

BACKGROUND

The known compound of formula (I), (3R,4R)-3-hydroxy-4-hydroxymethylpyrrolidine, is a key intermediate compound for the synthesis of certain of the applicant's inhibitor compounds, including potent PNP inhibitors (see for example PCT/NZ03/000186). The enantiomer of the compound for formula (I) is the compound of formula (Ia) and this is also useful as an intermediate for the synthesis of PNP inhibitors.

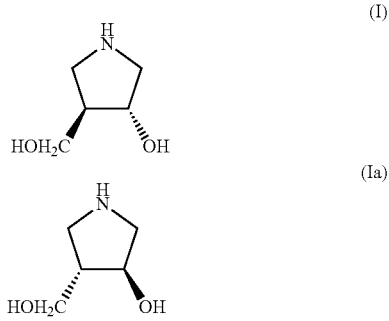

Makino and Ichikawa (K. Makino and Y. Ichikawa, *Tetrahedron Letters* (1998) 39, 8245) have reported a synthesis of compound (I). The requisite chirality of compound (I) is introduced using a Sharpless asymmetric epoxidation.

Karlsson and Högberg (S. Karlsson and H.-E. Högberg, *Tetrahedron: Asymmetry* (2001) 12, 1977) describe an alternative synthesis method. In this method, chirality is introduced using a chiral sultam auxiliary.

Galeazzi et al. (R. Galeazzi, G. Martelli, G. Mobbili, M. Orena and S. Rinaldi, *Tetrahedron: Asymmetry* (2004) 15, 3249) prepared compound (I) by the addition of (S)-1-phenylethylamine to an ethyl 2-silyloxy-3-methoxycarbonyl-but-3-enoate.

Filichev et al. (V. V. Filichev and E. B. Pedersen, *Tetrahedron* (2001) 57, 9163; V. V. Filichev, M. Brandt and E. B. Pedersen, *Carbohydrate Research* (2001) 333, 115) have used chiral starting materials to produce compound (I): For example, compound (I) can be prepared from diacetone-D-glucose or from D-xylose. However, both synthetic procedures are complex and require many reaction steps.

An alternative method for introducing chirality involves the use of biological catalysts. For example, Hansen and Bols (S. U. Hansen and M. Bols, *Acta Chemica Scandinavica* (1998) 52, 1214) attempted the enzymatic resolution of the N-Boc derivative of racemic trans-4-hydroxymethylpyrrolidin-3-ol using immobilised lipases from *Candida antarctica* and *Mucor mihei*. This method focuses on attempting to resolve the diol by enzymatic means. However, poor enantiomeric excesses were obtained in this way, resulting in only small amounts of compound (I) being made available for use as an intermediate in the preparation of other compounds. Low product yields mean considerable wastage and therefore high overall cost.

The published syntheses of compound (I) are deemed unsatisfactory as commercially viable routes to this valuable intermediate compound. There has been an ongoing need to overcome this problem by developing an improved method which employs only a few reaction steps and with an acceptable overall product yield.

It is known that lipase catalysed resolution of carbocyclic cis- and trans-β-hydroxy esters by O-acylation can provide enantiopure compounds in high yields (L. M. Levy, J. R. Dehli and V. Gotor, *Tetrahedron: Asymmetry* (2003) 14, 2053). However, it is very difficult to predict the reactivity of an enzyme to a potential substrate. The specificity of enzymes is well known in the art. Even when a particular compound is found to be an enzyme substrate there is often little certainty as to reaction yield and enantiomeric purity of the product.

The applicant has shown that compound (I) can be prepared in high yield and high enantiomeric excess from a (±)-trans-1-N-protected-4-hydroxypyrrolidine-3-carboxylic acid alkyl ester, via lipase catalysed esterification (WO 2005/033076). However, that preparation method suffers from several key disadvantages. In particular, the method requires chromatographic purification steps. Such steps are expensive processing steps. They add considerable cost to the overall method and they typically result in a lower yield of the compound. These disadvantages are especially apparent when the method is carried out on large scale. There has therefore been a need for an improved process for preparing the compounds of formulae (I) and (Ia) that avoids these disadvantages, particularly for the scale of process required for commercial production.

The applicant has now developed an improved method for preparing 3-hydroxy-4-hydroxymethylpyrrolidine compounds, using readily available starting materials. This new route overcomes the problems often encountered with syntheses that employ achiral starting materials. It involves fewer chemical transformations than published methods, and allows for the preparation of the desired compounds in high yield and enantiomeric excess. Most importantly, the improved method avoids the need for any chromatographic purification steps. This surprising discovery provides an advantage over known processes, including the process described in WO 2005/033076, that enables a significantly simpler and cost effective route to 3-hydroxy-4-hydroxymethylpyrrolidine compounds, and other compounds, such as PNP inhibitors, that may be prepared from them.

It is therefore an object of the invention to provide an improved method for preparing 3-hydroxy-4-hydroxymethylpyrrolidine compounds.

STATEMENTS OF INVENTION

In a first aspect the invention provides a process for preparing (3R,4R)-3-hydroxy-4-hydroxymethylpyrrolidine, the compound of formula (I), or (3S,4S)-3-hydroxy-4-hydroxymethylpyrrolidine, the compound of formula (Ia):

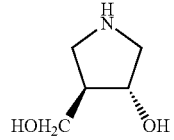
(I)

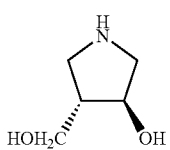
(Ia)

including the following steps:

step (a): enzyme-catalysed enantioselective hydrolysis of a racemic 3,4-trans-disubstituted pyrrolidinone compound of formula (II):

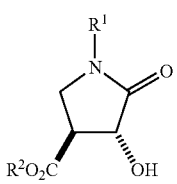
(II)

where $R^1$ is benzyl or benzhydryl, each of which may be optionally substituted by halogen, alkyl or alkoxy; and $R^2$ is aryl or straight or branched chain alkyl or aralkyl, any of which may be optionally substituted by halogen, alkyl or alkoxy;

to give either:

mixture (i): a 3,4-trans-disubstituted pyrrolidinone compound of formula (III) and unreacted pyrrolidinone compound of formula (IV):

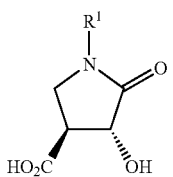
(III)

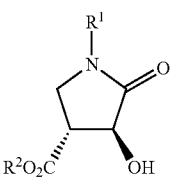
(IV)

where $R^1$ and $R^2$ are as defined above;

or mixture (ii): a 3,4-trans-disubstituted pyrrolidinone compound of formula (IIIa) and unreacted pyrrolidinone compound of formula (IVa):

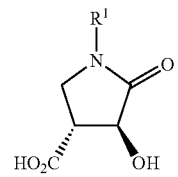
(IIIa)

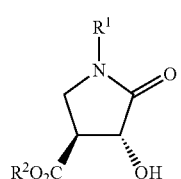
(IVa)

where $R^1$ and $R^2$ are as defined above;

where the enzyme-catalysed enantioselective hydrolysis is carried out using either an enzyme capable of producing an enantiomeric excess of compound (III), or an enzyme capable of producing an enantiomeric excess of compound (IIIa);

step (b): separation of the compound of formula (III) from the compound of formula (IV) in mixture (i), or separation of the compound of formula (IIIa) from the compound of formula (IVa) in mixture (ii); and step (c): transformation of the compound of formula (III) or the compound of formula (IVa) to the compound of formula (I), or transformation of the compound of formula (IV) or the compound of formula (IIIa) to the compound of formula (Ia).

It is preferred that the enzyme-catalysed enantioselective hydrolysis in step (a) is carried out using an enzyme capable of producing an enantiomeric excess of compound (III).

Preferably, where the enzyme-catalysed enantioselective hydrolysis in step (a) gives a mixture of compounds of formulae (III) and (IV), the enantiomeric excess of compound (III) is at least about 80%, most preferably at least about 90%. Alternatively, where the enzyme-catalysed enantioselective hydrolysis in step (a) gives a mixture of compounds of formulae (IIIa) and (IVa), the enantiomeric excess of compound (IIIa) is at least about 80%, most preferably at least about 90%.

It is further preferred that the enzyme used in the enzyme-catalysed enantioselective hydrolysis in step (a) is a lipase or an esterase. In one embodiment, the enzyme is a lipase, preferably from *Candida antarctica*. In another embodiment, the enzyme is an esterase, preferably a pig liver esterase.

It is preferred that where the compound of formula (III) is transformed to the compound of formula (I), the transformation is effected by a process including the step of reduction of the compound of formula (III) or formula (IIIa) to give a 3,4-trans-disubstituted pyrrolidine compound of formula (V) or formula (Va):

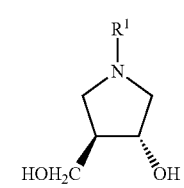
(V)

(Va)

[Structure: pyrrolidine with R¹ on N, HOH₂C and OH substituents]

where R¹ is as defined in above.

It is preferred that the reduction is carried out using lithium aluminium hydride or borane, most preferably borane.

Preferably the transformation further includes the step of replacement of the R¹ group of the compound of formula (V) or formula (Va) with hydrogen, to give the compound of formula (I) or formula (Ia). It is preferred that this is carried out by hydrogenolysis.

It is also preferred that the separation of the compound of formula (III) from the compound of formula (IV) in step (b) is carried out by extracting the compound of formula (IV) from an aqueous solution containing the compound of formula (IV) and a carboxylate salt form of the compound of formula (III) using a first water-immiscible solvent, then lowering the pH of the resulting mixture to convert the carboxylate salt form of the compound of formula (III) to the carboxylic acid form of the compound of formula (III), then extracting the resulting mixture again with a second water-immiscible solvent.

Preferably the water-immiscible solvent is dichloromethane or chloroform, and the second water-immiscible solvent is ethyl acetate.

Optionally, the compound of formula (I) or formula (Ia) may be converted to a 3,4-trans-disubstituted pyrrolidine compound of formula (VI) or formula (VIa):

(VI)

[Structure: pyrrolidine with R⁴ on N, HOH₂C and OH substituents]

(VIa)

[Structure: pyrrolidine with R⁴ on N, HOH₂C and OH substituents]

where R⁴ is an N-protecting group.

Preferably R⁴ is alkoxycarbonyl, aryloxycarbonyl or aralkoxycarbonyl. Most preferably R⁴ is tert-butoxycarbonyl, methoxycarbonyl or benzyloxycarbonyl.

Where R⁴ is alkoxycarbonyl, aryloxycarbonyl or aralkoxycarbonyl, it is preferred that compound of formula (I) is converted to the compound of formula (VI) by treatment of the compound of formula (I) with an alkoxycarbonylating agent, an aryloxycarbonylating agent or an aralkoxycarbonylating agent in the presence or absence of a base such as triethylamine or sodium hydroxide.

It is further preferred that the compound of formula (II) is prepared by a process including the step of reductive cleavage of the N—O bond of a 4,5-cis-disubstituted isoxazolidine compound of formula (VII), and in situ cyclisation to give the compound of formula (II):

(VII)

[Structure: isoxazolidine with R¹ on N, R²O₂C and CO₂R² substituents]

where R¹ and R² are as defined above.

Most preferably the compound of formula (VII) is prepared by 1,3-cycloaddition of a nitrone of formula (VII) and an alkene of formula (IX):

(VIII)

[Structure: nitrone with R¹ on N]

(IX)

[Structure: alkene with R²O₂C and CO₂R² substituents]

where R¹ and R² are as defined above.

Preferably the 1,3-cycloaddition is carried out by generating the nitrone of formula (VII) and then allowing it to react in situ with the alkene of formula (IX). Where R¹ is benzyl, it is preferred that the nitrone of formula (VIII) is generated by reaction of N-benzylhydroxylamine and HCHO.

It is preferred that R¹ is benzyl. It is further preferred that R² is alkyl. Most preferably R² is methyl or ethyl.

It is also preferred that the reductive cleavage and in situ cyclisation is carried out by hydrogenolysis or by using Zn in the presence of an acid.

It is preferred that the process of the invention further includes converting the compound of formula (I) or (Ia) to a compound of formula (X) or (Xa):

(X)

[Structure: pyrrolidine with H on N, R⁵H₂C and OH substituents]

(Xa)

[Structure: pyrrolidine with H on N, R⁵H₂C and OH substituents]

where R⁵ is selected from H, OH and SH, or from alkyloxy, aralkyloxy, aryloxy, alkylthio, aralkylthio, and arylthio each of which may be substituted by halogen, branched or straight chain saturated or unsaturated alkyl, alkoxy, aralkyloxy or aryloxy.

In a preferred embodiment the process of the invention also includes converting the compound of formula (I) or (Ia) to a compound of formula (X) or (Xa) and then reacting the compound of formula (X) or (Xa) with a compound of formula (XI) to give a compound of formula (XII) or (XIIa):

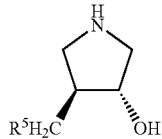
(X)

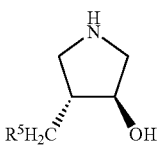
(Xa)

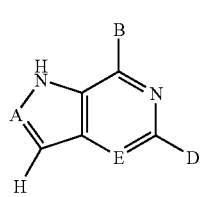
(XI)

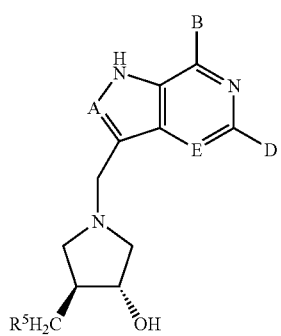
(XII)

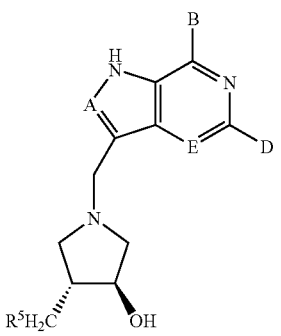
(XIIa)

where $R^5$ is as defined above;

A is selected from N, CH and $CR^6$, where $R^6$ is selected from halogen, OH and $NH_2$, or $R^6$ is selected from alkyl, aralkyl and aryl, each of which may be substituted by halogen, branched or straight chain saturated or unsaturated alkyl, alkoxy, aralkyloxy or aryloxy, or $R^6$ is selected from $NHR^7$, $NR^7R^8$ and $SR^9$, where $R^7$, $R^8$ and $R^9$ are selected from alkyl, aralkyl and aryl each of which may be substituted by halogen, branched or straight chain saturated or unsaturated alkyl, alkoxy, aralkyloxy or aryloxy;

B is selected from OH, $NH_2$, $NHR^{10}$, SH, hydrogen and halogen, where $R^{10}$ is selected from alkyl, aralkyl and aryl each of which may be substituted by halogen, branched or straight chain saturated or unsaturated alkyl, alkoxy, aralkyloxy or aryloxy;

D is selected from OH, $NH_2$, $NHR^{11}$, hydrogen, halogen and $SCH_3$, where $R^{11}$ is selected from alkyl, aralkyl and aryl each of which may be substituted by halogen, branched or straight chain saturated or unsaturated alkyl, alkoxy, aralkyloxy or aryloxy; and E is selected from N and CH.

Preferably the reaction is carried out using formaldehyde or a formaldehyde equivalent.

In an alternative embodiment the compound of formula (XI) is converted into a compound of formula (XIII) and then reacting the compound of formula (X) or (Xa) with a compound of formula (XIII) to give a compound of formula (XII) or (XIIa):

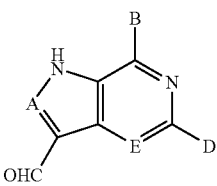
(XIII)

where A, B, D and E are as defined above each of which, and the NH in the 5-membered ring, may be protected with suitable protecting groups.

Preferably the process of the invention further includes preparing the compound of formula (II) and further includes converting the compound of formula (I) or (Ia) to a compound of formula (X) or (Xa):

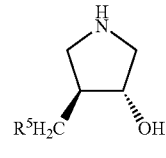
(X)

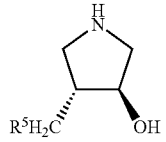
(Xa)

where $R^5$ is selected from H, OH and SH, or from alkyloxy, aralkyloxy, aryloxy, alkylthio, aralkylthio, and arylthio each of which may be substituted by halogen, branched or straight chain saturated or unsaturated alkyl, alkoxy, aralkyloxy or aryloxy.

Preferably the process further includes reacting the compound of formula (X) or (Xa) with a compound of formula (XI) to give a compound of formula (XII) or (XIIa):

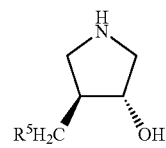
(X)

-continued (Xa)
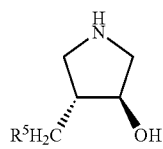

(XI)
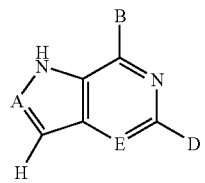

(XII)
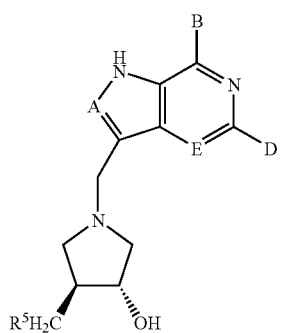

(XIIa)
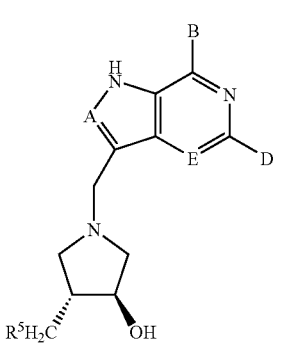

where $R^5$, A, B, D and E are as defined above.

In one preferred embodiment, the invention provides a process for preparing (3R,4R)-3-hydroxy-4-hydroxymethylpyrrolidine, a compound of formula (I) or (3S,4S)-3-hydroxy-4-hydroxymethylpyrrolidine, a compound of formula (Ia):

(I)
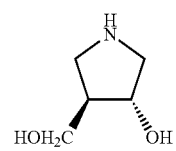

(Ia)
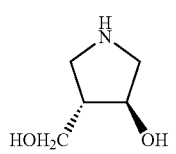

including the steps of:

(i) 1,3-cycloaddition of a nitrone of formula (2) and an alkene of formula (3) to give a 4,5-cis-disubstituted isoxazolidine compound of formula (4):

(2)

(3)
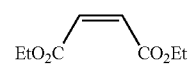

(4)
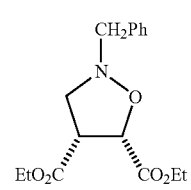

(ii) reductive cleavage of the N—O bond of the 4,5-cis-disubstituted isoxazolidine compound of formula (4) and in situ cyclisation to give a 3,4-trans-disubstituted pyrrolidinone compound of formula (5):

(5)
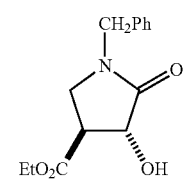

(iii) enzyme-catalysed enantioselective hydrolysis of the compound of formula (5) to give a mixture of a compound of formula (6), and unreacted compound of formula (5), or a mixture of a compound of formula (6a), and unreacted compound of (6)

(5)

(6a)

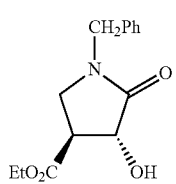
(5a)

(iv) separation of the compound of formula (6) from the compound of formula (5), or separation of compound of formula (6a) from the compound of formula (5a);

(v) reduction of the compound of formula (6) or (5a) to give a compound of formula (7), or reduction of the compound of formula (6a) or (5) to give a compound of

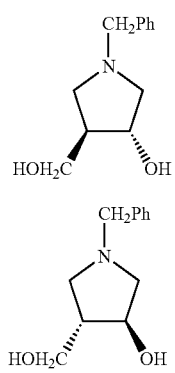
(7)

(7a)

(vi) replacement of the CH$_2$Ph group with hydrogen in the compound of formula (7) to give the compound of formula (I), or replacement of the CH$_2$Ph group with hydrogen in the compound of formula (7a) to give the compound of formula (Ia).

In another embodiment the process includes the step of:

(vii) conversion of the compound of formula (I) to a compound of formula (8), or conversion of the compound of formula (Ia) to a compound of formula (8a):

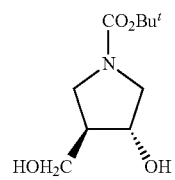
(8)

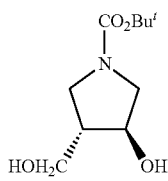
(8a)

by treatment of the compound of formula (I), or the compound of formula (Ia) with di-tert-butyldicarbonate or di-tert-butyldicarbonate.

The compound of formula (I), or the compound of formula (Ia), is optionally not isolated, and the conversion of the compound of formula (I) to the compound of formula (8), or the compound of formula (Ia) to the compound of formula (8a), in step (vii) is effected in situ.

The invention also provides (3R,4R)-3-hydroxy-4-hydroxymethylpyrrolidine, when prepared by the process of the invention, and (3S,4S)-3-hydroxy-4-hydroxymethylpyrrolidine, when prepared by the process of the invention.

The invention further provides a compound of formula (XII), when prepared by the process of the invention, and a compound of formula (XIIa), when prepared by the process of the invention.

The invention further provides a compound of formula (III):

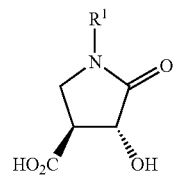
(III)

where R$^1$ is as defined above.

The invention also provides a compound of formula (IV):

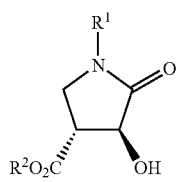
(IV)

where R$^1$ and R$^2$ are as defined above.

DETAILED DESCRIPTION

The invention provides a convenient route to (3R,4R)-3-hydroxy-4-hydroxymethylpyrrolidine as well as its enantiomer (3S,4S)-3-hydroxy-4-hydroxymethylpyrrolidine, both of which are useful for the synthesis of certain potent enzyme inhibitors.

According to the process of the invention, chirality is conveniently introduced using a biological catalyst, and no chromatographic purification is required at the resolution step. The process advantageously provides a route to compounds of formula (III), which are intermediates for the preparation of (3R,4R)-3-hydroxy-4-hydroxymethylpyrrolidine. It also provides a route to compounds of formula (IIIa), which are intermediates for the preparation of (3S,4S)-3-hydroxy-4-hydroxymethylpyrrolidine. Another advantage of this process is that it readily provides a route to compounds of formulae (IV) and (IVa). Compounds of formulae (IV) and (IVa) may find use in other applications.

Advantageously, compounds (III) and (IV) are produced in high yields with excellent enantioselectivity, and are readily separated.

A further advantage of the process is that, depending upon selection of the enzyme, the process can also provide a route to compound (IVa), which may also be readily separated from the compound of formula (IIIa) and transformed to the desired compound, (3R,4R)-3-hydroxy-4-hydroxymethylpyrrolidine.

It will be understood by those skilled in the art that racemic mixtures of the 4,5-cis-disubstituted isoxazolidine compounds of formula (VII) and the 3,4-trans-disubstituted pyrrolidinone compounds of formula (II) are obtained according to the invention. Advantageously, readily available starting materials may be used to initially produce compounds of formula (II) in only two steps, and in high yield. The subsequent enantioselective hydrolysis of a compound of formula (II) provides pure enantiomeric forms, or at least mixtures highly enriched in one enantiomer.

It will also be clear to those skilled in the art that the groups $R^1$ and $R^2$, as defined above, may themselves be optionally substituted. For example, $R^2$ may be substituted with one or more substituents selected from halogen and straight or branched chain alkyl or alkoxy. Similarly, $R^1$ may be substituted with halogen or straight or branched chain alkyl or alkoxy, for example, p-methoxy.

It will be appreciated that representations of any compounds having substituents B and D, and where B and/or D is a hydroxy group, are of the enol-type tautomeric form of a corresponding amide, and will largely exist in the amide form. The use of the enol-type tautomeric representation is simply to allow fewer structural formulae to represent the compounds of the invention.

Similarly, it will be appreciated that representations of any compounds having substituents B and D, and where B and/or D is a thiol group, are of the thioenol-type tautomeric form of a corresponding thioamide, and will largely exist in the thioamide form. The use of the thioenol-type tautomeric representation is simply to allow fewer structural formulae to represent the compounds of the invention.

Although it is preferred that the compound of formula (VI) incorporates a tert-butoxycarbonyl N-protecting group, it will be clear to the skilled person that other N-protecting groups may be employed (see for example, "Protective Groups in Organic Synthesis" by Theodora W. Greene and Peter G. M. Wuts, Wiley-Interscience, 3rd edition (May 15, 1999)). Other suitable protecting groups include alkoxycarbonyl, aryloxycarbonyl, aralkoxycarbonyl, acyl or sulfonyl derivatives.

As used herein, the structural formulae showing the "wedge" notation, e.g.:

are intended to represent pure enantiomeric forms of a trans isomer.

Similarly, the structural formulae showing the "rectangular" notation, e.g.:

are intended to represent racemic mixtures of trans isomers.
Synthesis of Compounds In a preferred embodiment of the invention (Scheme 1), compound (+)-8 is prepared from diethyl maleate 3 and nitrone 2. The sequential cycloaddition, reductive cleavage and rearrangement steps shown in Scheme 1 efficiently provide the pure trans-substituted pyrrolidinone (±)-5, which has previously been obtained only by fractional crystallisation of a cis-trans mixture (Kametani, T., Kigawa, Y., Ihara, M. *Tetrahedron*, 1979, 35, 313-316).

The 1,3-cycloaddition reaction of nitrones, such as 2, with alkenes, leading to isoxazolidines is a reaction known to those skilled in the art. This cycloaddition proceeds in a specifically cis fashion so that the relative stereochemistry at C-4 and C-5 of the isoxazolidine is always controlled by the geometric relationship of the substituents on the alkene.

Reductive cleavage of the N—O bond of isoxazolidines, most commonly by hydrogenolysis or with zinc and acid, gives β-amino alcohols. The amino alcohols derived from 5-alkoxycarbonyl isoxazolidines readily cyclise to pyrrolidinones, with no epimerisation at C-4 or C-5 (isoxazolidine numbering). Thus, a 4,5-cis-disubstituted isoxazolidine gives rise to a 3,4-trans-disubstituted pyrrolidinone.

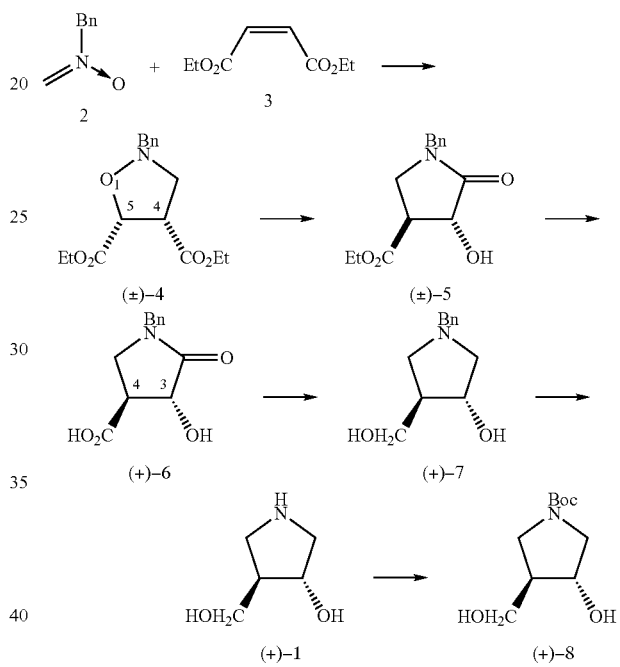

Scheme 1

The products (±)-4 and (±)-5 of the above chemistry are racemic mixtures. The use of enantioselective hydrolysis provides pure enantiomeric forms, or at least mixtures highly enriched in one enantiomer [(+)-6, (+)-7, (+)-1, (+)-8]. Consequently this process is suitable for use in the construction of pharmaceutical products.

Lipases are commonly used for the stereoselective and enantioselective hydrolyses of esters (Faber, K. *Biotransformations in Organic Chemistry*. Springer-Verlag, Berlin, 2004, 94-119). The B-lipase from the yeast *Candida antarctica* (CALB) has recently been shown to be a particularly efficient and robust enzyme, catalysing a great number of enantioselective reactions (Faber, K. *Biotransformations in Organic Chemistry*. Springer-Verlag, Berlin, 2004, 94-119; Anderson, E. M., Larson, K. M.; Kirk, O. *Biocatalysis Biotransformation*, 1997, 16, 181-204).

Immobilized forms of CALB, such as the commercially available product Novozyme® 435, have enhanced stability and are easily separated from the reaction products (Anderson, E. M., Larson, K. M.; Kirk, O. *Biocatalysis Biotransformation*, 1997, 16, 181-204).

The process of the invention preferably uses Novozyme® 435 to resolve racemic ester (±)-5. Enantioselective hydrolysis yields the (+)-(3R,4S)-acid 6 in good yield (36-45% based on the racemate) and excellent enantiomeric excess (94-96%), together with the ester (−)-5 (ee >97%).

Reduction of carboxylic acid and lactam moieties is most commonly achieved using either lithium aluminium hydride or borane (Barrett, A. G. M., in *Comprehensive Organic Synthesis*, (Ed. Trost, B. M. and Fleming, I), Pergamon, Oxford, 1991, 8, 237-238 and 249-251).

The applicant has found the in situ generation of borane from sodium borohydride using boron trifluoride diethyl ether complex to be a convenient method for the reduction of (+)-6 to the N-benzylpyrrolidine (+)-7, which is then converted to (+)-1 by hydrogenolysis. The corresponding Boc-carbamate (+)-8 can be formed by various methods known to those skilled in the art. In the preferred embodiment of the invention, di-tert-butyl-dicarbonate and a base such as sodium hydroxide or triethylamine in methanol are used in this step.

Advantageously, the new process for the synthesis of (3R,4R)-3-hydroxy-4-hydroxymethylpyrrolidine includes fewer chemical transformations than previously known methods. The desired compounds are obtained in high yields. In addition, the process avoids or reduces the use of chromatographic purification which is problematic when larger quantities (e.g. kilograms) are required, making the process highly suitable for scale-up in the preparation of large amounts of compounds for pharmaceutical use.

A further advantage of the present process is that the N-benzylpyrrolidine (+)-7 can be crystallised thereby further improving the enantiomeric excess. In addition, compound (+)-1 can readily be converted to a crystalline material, the N-tert-butoxycarbonyl derivative (+)-8. Compound (+)-(8) is a very stable intermediate and is conveniently converted back to (3R,4R)-3-hydroxy-4-hydroxymethylpyrrolidine (+)-1 by simple acid treatment.

Optionally, recrystallisation steps may be added in order to enhance the enantiomeric purity of the desired compounds.

Processes for the use of the compounds of formula (I) or (Ia) as intermediates in the preparation of PNP inhibitors are described in detail in WO 2004/018496 (PCT/NZ2004/000186) and WO 2004/069856 (PCT/NZ2004/000017).

Screening of Hydrolases

The screening methodology set out below enables a person to determine whether any enzyme will be effective for the enzymatic resolution step of this invention. It is to be appreciated therefore that the invention is not limited to any specific enzyme described or claimed. The methodology enables to person to select any enzyme from a group, screen the enzyme for desirable yield and enantiomeric excess, and use that enzyme in the process of the invention or select an alternative enzyme.

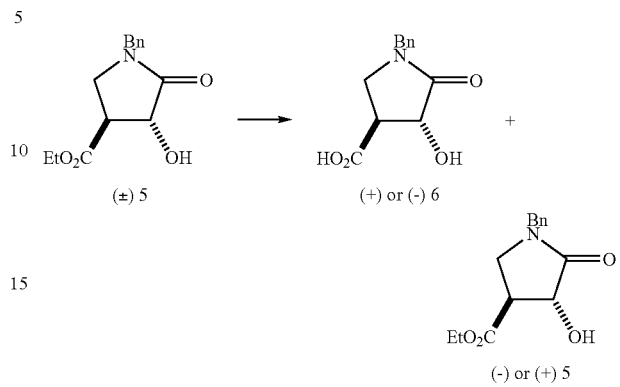

A total of twenty two lipases, esterases, and proteases (Table 1) were tested for their ability to catalyse the hydrolysis depicted in Scheme 1. Each enzyme (5-50 mg, Table 1) was stirred with racemic ester (±)-5 (50 mg), methyl tert-butyl ether (MTBE, 0.1 mL), phosphate buffer (0.1 M, pH 7.5, 0.1 mL), water (1 mL) and phenol red indicator. As hydrolysis proceeded, the product acid (6) was titrated with sodium hydroxide (0.1 M) to the phenol red end point. Thus the consumption of sodium hydroxide is a measure of the extent of reaction. Fifteen of the enzymes were unable to achieve 10% conversion over 24 h so were discarded. The remaining seven reactions were subjected to an extractive work up, either when 50% conversion had been reached [pig liver esterase (PLE), subtilisin, Novozyme 435] or when no further conversion was observed (pancreatin, *Pseudomonas* sp. lipoprotein lipase, *Chromobacterium viscosum* lipoprotein lipase, Lipozyme). The extracts, which contain both ester 5 and acid 6, were treated with trimethylsilyldiazomethane in order to convert the acid to the corresponding methyl ester. The enantiomeric purity of 5 and 6 could then be determined by HPLC (Chiracel OD-H). Pig liver esterase, Novozyme 435 and pancreatin yielded 5 and 6 with moderate to high enantiomeric excesses (Table 1), but pancreatin reacted only very slowly at high enzyme loadings. The first two of these enzymes were therefore selected for further study. They each preferentially hydrolyse a different enantiomer of ester 5. Novozyme 435 gives (+) acid 6 and (−) ester 5 whilst PLE gives (−) 6 and (+) 5.

TABLE 1

Screening of enzymes for their utility as catalysts of the enantioselective hydrolysis of racemic ester 6

| | Enzyme | Quantity (mg, μL) | Time (h) | Extent of reaction (%) | E.E. of ester | E.E. of acid | Enantiomer converted |
|---|---|---|---|---|---|---|---|
| Esterases | Pig Liver Esterase (PLE) | 20 | 0.25 | 51 | 77.9 | 72.9 | (−) |
| Proteases | Papain | 50 | 22 | <10 | n.d. | n.d. | |
| | Subtilisin | 12 | 0.8 | 48 | 11.3 | 18.3 | (+) |
| Lipases | Novozyme 435 | 5 | 6 | 51 | 85.3 | 71.1 | (+) |
| | Pancreatin | 49 | 31.6 | 39 | 92.0 | 79.1 | (−) |
| | *Pseudomonas* sp. lipoprotein lipase | 17 | 10.5 | 45 | 44.0 | 45.4 | (−) |
| | *Chromobacterium viscosum* lipoprotein | 14 | 48 | 36 | 40.6 | 61.4 | (−) |
| | Lipozyme | 49 | 30 | 38 | 0.6 | 24.3 | (+) |

TABLE 1-continued

Screening of enzymes for their utility as catalysts of the enantioselective hydrolysis of racemic ester 6

| Enzyme | Quantity (mg, μL) | Time (h) | Extent of reaction (%) | E.E. of ester | E.E. of acid | Enantiomer converted |
|---|---|---|---|---|---|---|
| *Candida cylindracea* lipase, immobilized on Sol-Gel | 46 | 28 | <10 | n.d. | n.d. | |
| *Aspergillus niger* lipase, immobilized on Sol-Gel | 48 | 28 | <10. | n.d. | n.d. | |
| *Pseudomonas cepacia* lipase, immobilized on ceramic | 49 | 28 | <10 | n.d. | n.d | |
| Novozyme 871 | 50 | 23 | <10. | n.d. | n.d. | |
| *Rhizopus arrhizus* lipase | 50 | 23 | <10 | n.d. | n.d. | |
| *Candida lipolytica* lipase | 37 | 23 | <10 | n.d. | n.d. | |
| *Mucor javanicus* lipase | 38 | 23 | <10 | n.d. | n.d. | |
| *Penicillum roqueforti* lipase | 33 | 23 | <10 | n.d. | n.d. | |
| Wheat Germ lipase | 31 | 23 | <10 | n.d. | n.d. | |
| *Aspergillus oryzae* lipase | 32 | 23 | <10 | n.d. | n.d. | |
| *Rhizimucor miehei* lipase | 21 | 23 | <10 | n.d. | n.d. | |
| *Psuedomonas fluorescens* lipase | 19 | 23 | <10 | n.d. | n.d. | |
| *Psuedomonas* sp. 2 lipoprotein lipase | 1 | 48 | <10 | n.d. | n.d. | |
| *Candida rugosa* lipase | 25 | 24 | <10 | n.d. | n.d. | |

PLE catalyzed the hydrolysis of 5 in the presence of several cosolvents. The enantiomeric excess of the recovered ester and acid was largely independent of the cosolvent (Table 2). If the hydrolysis reaction was allowed to proceed to 70% completion, the unreacted ester (+)-5 was obtained in excellent enantiomeric excess (Table 3), but with concomitant reduction in yield.

TABLE 2

Hydrolyses with PLE utilising different cosolvents

| Cosolvent[a] | Mass PLE (mg) | Time (min) | Extent of reaction (%) | E.E. of ester (%) | E.E. of acid (%) |
|---|---|---|---|---|---|
| MTBE | 4.4 | 80 | 49 | 76.2 | n.d. |
| Acetone | 4.4 | 105 | 52 | 77.3 | 64.8 |
| Toluene | 4.6 | 70 | 53 | 75.7 | 56.8 |
| Dichloromethane | 4.8 | 40 | 52 | 80.4 | 68.7 |

[a]Reactions were carried out as described in 'Screening of Hydrolases' except that other solvents were substituted for MTBE.

TABLE 3

Hydrolyses with PLE beyond 50% completion.

| Cosolvent[a] | Mass PLE (mg) | Extent of reaction (%) | E.E. of ester (%) |
|---|---|---|---|
| Acetone | 4.4 | 52 | 77.3 |
| Toluene | 4.6 | 53 | 75.7 |
| Acetone | 4.8 | 59 | 83.7 |
| Toluene | 4.7 | 60 | 88.0 |
| Acetone | 4.6 | 71 | 92.5 |
| Toluene | 4.6 | 70 | 94.5 |

[a]Reactions were carried out as described in 'Screening of Hydrolases' except that reactions were allowed to proceed past 50% complete.

Novozyme 435 resolved (±)-5 in to acid (+)-6 and ester (−)-5, each in good e.e. (~95%), both without any co-solvent and in the presence of acetone. Ester 5 was reduced with borane-dimethyl sulfide complex to the N-benzyl-pyrrolidine 7 in moderate yield.

EXAMPLES

The invention is further described with reference to the following examples. It is to be understood that the invention is not limited to these examples.

Example 1

(±)-2-N-Benzyl-isoxazolidine-4,5-cis-dicarboxylic acid diethyl ester [(±)-4]

N-Benzylhydroxylamine hydrochloride (144.8 g, 0.91 mol) and anhydrous sodium acetate (82 g, 1 mol) were stirred together in ethanol (800 mL) at ambient temperature for 30 minutes after which time 37% aqueous formaldehyde (134 mL, 1.8 mol) was added and stirring was continued for 1 hour. Diethyl maleate 3 (134 mL, 0.83 mol) was added and the mixture stirred for 1 h followed by heating under reflux for 2 h. After cooling, the mixture was filtered, the filtrate evaporated and the residue taken up in ethyl acetate (1.5 L) and washed three times with saturated sodium bicarbonate (200 mL each). The organic layer was removed and dried ($MgSO_4$) and the solvent evaporated to give the crude product (±)-4 as a yellow oil (250.3 g, 98% based on amount of diethyl maleate). A small amount was purified by column chromatography on silica (eluent: EtOAc:hexanes, 2:8 v/v) and the analytical data is as follows: $^1$H NMR ($CDCl_3$) δ ppm: 7.40-7.20 (m, 5H), 4.76 (br. d, 1H), 4.29-4.08 (m, 5H), 4.02 (br. d, 1H), 3.77 (q, 1H, J=8.7 Hz), 3.60-3.00 (br. m, 2H), 1.28 (t, 3H, J=7.2 Hz), 1.25 (t, 3H, J=7.2 Hz). $^{13}$C NMR ($CDCl_3$) δ ppm: 169.7 (s), 169.1 (s), 136.4 (s), 129.0 (d), 128.4 (d), 127.6 (d), 77.0 (d), 62.5 (t), 61.4 (t), 61.3 (t), 56.8 (br. t), 50.4 (br. d), 14.0 (q). EIMS (+ve): m/z Calcd. for $C_{16}H_{21}NO_5$ $(M)^+$ 307.14197; Found: 307.14184.

Example 2

(±)-trans-1-N-Benzyl-3-hydroxy-2-pyrrolidinone-4-carboxylic acid ethyl ester [(±)-5)]

To a solution of crude 2-N-benzyl-isoxazolidine-4,5-cis-dicarboxylic acid diethyl ester (±)-4 (250.3 g, 0.81 mol) in acetic acid (2 L) was added in one portion powdered zinc (106 g, 1.62 mol). An ice-water bath was used for a few minutes to control the very mild exotherm. The mixture was stirred for 15 minutes then filtered through Celite. The solvent was evaporated, the residue taken up in dichloromethane (1.5 L) and washed with 300 mL batches of a saturated solution of sodium bicarbonate until no more degassing was observed. The organic layer was removed and dried ($MgSO_4$) and the solvent evaporated to give the crude product (±)-5 as a light brown oil (193.6 g, 91%). A small amount was purified by column chromatography on silica (eluent: ethyl acetate:hexanes, 1:1 v/v) and the analytical data is as follows: M.p. 65-66° C. (ethyl acetate-hexanes), Lit. 62-63.5° C. $^1$H NMR ($CDCl_3$) δ ppm: 7.38-7.19 (m, 5H), 4.67 (dd, 1H, J=8.3, 3.4 Hz, became a d, J=8.5 Hz on $D_2O$ exchange), 4.62 (d, 1H, J=3.5 Hz, disappeared on $D_2O$ exchange), 4.53 (d, J=14.6 Hz, A of AB system), 4.42 (d, 1H, J=14.7 Hz, B of AB system), 4.19 (q, 2H, J=7.1 Hz), 3.44 (t, 1H, J=9.6 Hz), 3.34 (t, 1H, J=9.2 Hz), 3.14 (q, 1H, J=8.8 Hz), 1.26 (t, 3H, J=7.1 Hz). $^{13}$C NMR ($CDCl_3$) δ ppm: 172.9 (s), 171.4 (s), 135.1 (s), 128.9 (d), 128.2 (d), 128.0 (d), 72.3 (d), 61.5 (t), 47.0 (t), 46.1 (d), 45.1 (t), 14.1 (q). EIMS: m/z Calcd. for $C_{14}H_{17}NO_4$ (M)$^+$ 263.11576. Found: 263.11538.

Example 3

(3R,4S)-1-N-Benzyl-3-hydroxy-2-pyrrolidinone-4-carboxylic acid [(+)-6] and (3S,4R)-1-N-Benzyl-3-hydroxy-2-pyrrolidinone-4-carboxylic acid ethyl ester [(−)-5]

A suspension of crude ester (±)-5 (191.8 g, 0.72 mol) in potassium phosphate buffer (0.1 M, 0.1 M NaCl, pH 7.5, 10 L) was stirred over Novozyme® 435 (20.0 g) for 5 h at 25° C. The enzyme was removed by filtration and the filtrate saturated with sodium chloride. Unreacted ester (−)-5 was removed by extraction with chloroform (3×5 L). The aqueous mixture was then brought to pH 1 with HCl (6 N) and further extracted with chloroform (9×5 L). The aqueous phase was then extracted with half the volume of EtOAc. The combined extracts were dried ($MgSO_4$) and concentrated under reduced pressure to give the crude title compound (+)-6 as a light brown solid (66.7 g, 39%). The analytical data for (+)-6 (yield: 1.78 mmol, 44%) and (−)-5 (yield: 1.85 mmol, 46%) derived from the enzymatic hydrolysis of a small batch (3.95 mmol) of chromatographically purified (±)-5 are as follows:

Analytical data for (+)-6: m.p. (ethylacetate) 144-146° C. [α]$^{20}_D$ +62.3 (c=1, EtOH). Enantiomeric excess (HPLC of methyl ester on Chiralcel OD-H) 94.8%. $^1$H NMR ($CDCl_3$): δ ppm: 7.37-7.21 (5H, bm), 4.76 (4H, bs, 2×OH, $H_2O$) 4.70 (1H, d, J=8.2 Hz), 4.46 (2H, dd, J=4.6, 10.3), 3.44 (2H, m), 3.19 (1H, m). $^{13}$C NMR ($CDCl_3$): δ ppm: 174.7, 173.8, 135.1, 129.3, 128.6, 128.5, 72.6, 47.6, 46.1, 45.5. Analysis: Found, C, 61.36; H, 5.56; N, 5.92. $C_{12}H_{13}NO_4$ requires C, 61.27; H, 5.57; N, 5.95.

Analytical data for (−)-5: [α]$^{20}_D$ −46.8 (c=1.1, EtOH). Enantiomeric excess (HPLC on Chiralcel OD-H) 97.7%.

Example 4

(3R,4R)-1-N-Benzyl-3-hydroxy-4-hydroxymethyl-pyrrolidine [(+)-7]

$BF_3.OEt_2$ (170 mL, 1382 mmol) was added dropwise to a suspension of acid (+)-6 (62 g, 264 mmol) and $NaBH_4$ (40 g, 1057 mmol) in THF (1 L) at 0° C. The mixture was left for 72 h. The reaction was then quenched with MeOH (500 mL) under ice-cooling (degassing) and the solvent evaporated. The residue was then treated with 6 N aqueous HCl (1 L) for 10 min followed by evaporation. NaOH (15% aqueous solution, 250 mL) was added until ph 12-14. The resulting solution was concentrated under vacuum to a solid which was then suspended in chloroform (1 L). Following filtration through celite the filtrate was evaporated to dryness to afford an oil which slowly crystallised on chasing with toluene. Further drying under vacuum gave compound (+)-7 as a white crystalline solid (54 g, 261 mmol, 99% yield). [α]$^{20}_D$ +37.3 (c=1, MeOH), m.p. 54-56° C.

Example 5

(3R,4R)-1-N-tert-Butoxycarbonyl-3-hydroxy-4-hydroxymethyl-pyrrolidine [(+)-8]

Crude (+)-7 from the previous step (60 g) was taken up in methanol (800 mL), 10% Pd/C (12 g, wet Degussa type) added and the mixture stirred under an atmosphere of hydrogen for 12 h to give crude (3R,4R)-3-Hydroxy-4-hydroxymethyl-pyrrolidine (+)-1. The catalyst was removed by filtration and to the solution in methanol was added triethylamine (30 mL, 216 mmol) and di-tert-butyl dicarbonate (47.5 g, 218 mmol) and the mixture was stirred at room temperature for 1 h (slight exotherm). The mixture was then preabsorbed onto silica and chromatographed by dry-flash chromatography (eluant: $CHCl_3$:EtOAc:MeOH, 5:2:1 v/v/v) to give (+)-8 as a light orange syrup (25.4 g, 59% from (+)-6). The final product contained about 15% (w/w) of a triethylammonium salt which could be removed by column chromatography on silica (hexanes:ethyl acetate, 1:4). The data for fully purified (+)-8 is as follows: [α]$^{20}_D$ +15.4 (c=0.5, MeOH). $^1$H NMR (MeOH-$d_4$): δ ppm: 4.14 (m, 1H), 3.58-3.45 (m, 4H), 3.24-3.18 (m, 2H), 2.24 (m, 1H), 1.46 (s, 9H). $^{13}$C NMR (MeOH-$d_4$): δ ppm (some peaks are doubled due to slow interconversion of rotamers): 156.99, 81.31, (73.10, 72.40), 63.06, (54.45, 54.03), (50.42, 49.75), (48.47, 48.03), 29.18.

Example 6

(3S,4R)-3-Hydroxy-4-(methylthiomethyl)-pyrrolidine

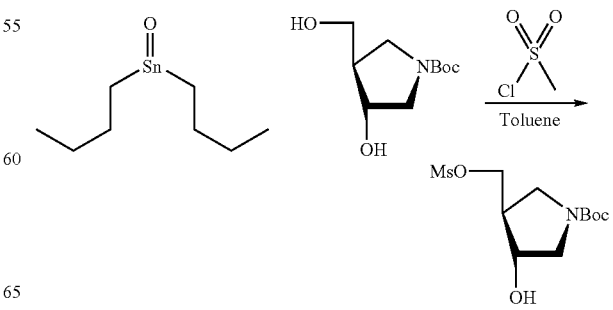

The protected amine (7.75 g, 35.7 mmol) and dibutyltin oxide (10.66 g, 42.8 mmol) were suspended in toluene (10 mL) and heated to reflux under Dean and Stark conditions. The reaction became homogeneous at around 100° C. The solution was heated under reflux for a further 1.5 h, cooled to −10° C. and then methanesulfonyl chloride (3.34 ml, 42.8 mmol) was added. The progress of the reaction was monitored using thin layer chromatography (TLC). After 1 h the reaction appeared incomplete and was allowed to warm to room temperature with stirring and left overnight, when the reaction appeared complete. Column chromatography of the solution directly loaded onto a column of silica gel eluted with 5% v/v MeOH in dichloromethane afforded the mesylate (10.0 g, 33.9 mmol, 95% yield) as a colourless oil.

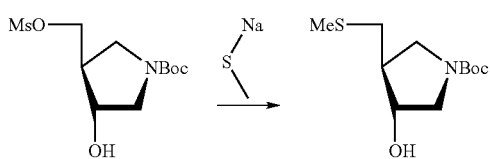

The mesylate (10 g, 33.9 mmol) was dissolved in DMF and sodium thiomethoxide (4.75 g, 67.7 mmol) was added portionwise. The solution was stirred overnight, diluted with toluene, washed with water and brine, dried ($MgSO_4$) and concentrate in vacuo. Column chromatography on silica gel (eluent 5% v/v MeOH in dichloromethane) afforded the N-protected 3-hydroxy-4-(methylthiomethyl)-pyrrolidine (8.2 g, 33.2 mmol, 98% yield) as a yellow oil.

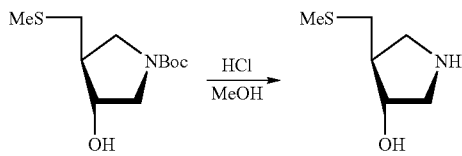

N-Protected 3-hydroxy-4-(methylthiomethyl)-pyrrolidine (8.2 g, 33.2 mmol) was dissolved in methanol (40 mL, 33.2 mmol) and to this was added hydrochloric acid (10 mL, 326 mmol) and the resulting solution concentrated in vacuo. This step was repeated, whereupon TLC (10% v/v 7N $NH_3$ in MeOH-dichloromethane) indicated complete deprotection. Column chromatography on silica eluted with 10-20% 7N $NH_3$ in MeOH-dichloromethane afforded the title compound (4.3 g, 29.2 mmol, 88% yield).

Example 7

Screening of Hyrolases

Racemic ester (±)-5 (50±5 mg, 0.2 mmol) was stirred with MTBE (0.1 mL) in a test tube and then phosphate buffer (0.1 M, with 0.1 M NaCl, pH 7.5, 0.1 mL), water (1.0 mL) and phenol red solution (0.1% in water, 0.01 mL) were added. Enzyme preparation (5-50 mg) was added to initiate the reaction, and NaOH (0.1 M) was added from a syringe as needed to maintain the indicator at a pinkish red. When 1.0±0.1 mL of NaOH solution (indicating approximately 50% hydrolysis) had been consumed (or after 23 h, or when the reaction appeared to have ceased) the reaction was stopped by addition of HCl (1 M) to pH 1 and the enzyme preparation was removed by filtration or by centrifugation. The filtrate or supernatant was saturated with NaCl (approx 750 mg) and extracted with EtOAc (3×1 mL). The dried ($MgSO_4$) extracts were concentrated under reduced pressure and taken up in dry methanol (2 mL). This solution was cooled under argon in an ice-water bath and trimethylsilyidiazomethane (2.0 M in hexane) was added until the yellow colour of the reagent persisted. The solution was stirred and room temperature for 5 min and then concentrated under reduced pressure. The resulting mixture of ethyl and methyl esters was analysed by HPLC using a Chiracel OD-H column eluted with hexane-isopropanol.

Example 8

Hydrolyses with Pig Liver Esterase (PLE)

Method (a).—A solution of ester (±)-5 (0.5 g, 1.98 mmol) in toluene (0.2 mL) was stirred with phosphate buffer (1.0 M, pH 7.5, 2.0 mL) and PLE (5 mg) for 54 h. The reaction mixture was diluted with acetone and filtered through a pad of Celite on a Whatman 50 filter paper. The filtrate was extracted three times with ethyl acetate and the combined extracts dried ($MgSO_4$) and concentrated under reduced pressure to give (+)-5 (0.25 g, 50%, 84% e.e.).

Method (b).—A solution of racemic ester (±)-5 (50 mg, 0.2 mmol) in toluene (0.1 mL) was stirred with phosphate buffer (0.1 M, with 0.1 M NaCl, pH 7.5, 0.1 mL), water (1.0 mL), phenol red solution (0.1% in water, 0.01 mL) and PLE (4.6 mg). NaOH (0.1 M) was added from a syringe as needed to maintain the indicator at a pinkish red. When 1.4 mL of NaOH solution had been consumed (indicating approximately 70% conversion) the reaction mixture was diluted with acetone and filtered through a pad of Celite on a Whatman 50 filter paper. The filtrate was extracted three times with ethyl acetate and the combined extracts dried ($MgSO_4$) and concentrated under reduced pressure to give (+)-5 (10 mg, 93% e.e.)

Example 9

Hydrolysis with Novozyme 435 Using Acetone as a Cosolvent

The crude ester (±)-5 (319 g, 1.21 mol) was dissolved in acetone (320 mL) and to this solution was added $K_2HPO_4$ buffer (3.2 L, 0.5 M, using a pH meter to adjust the pH to 7.5 with 0.5 M $KH_2PO_4$). Novozyme® 435 (30.0 g) was added and the resulting suspension was stirred for 6 h at 27° C. The enzyme was then removed by filtration through Celite and the residue washed with $K_2HPO_4$ buffer (300 mL). The filtrate was saturated with NaCl (~750 g) and the unreacted ester (−)-5 removed by extraction with chloroform (3×400 mL). The aqueous mixture was then brought to pH 1 with cHCl (150 mL, 12 N), resaturated with NaCl (100 g) and further extracted with ethyl acetate (6×400 mL). The combined extracts were dried ($MgSO_4$) and concentrated under reduced pressure to give the crude title compound (+)-6 as an off white solid which was crystallised from ethyl acetate to afford (+)-6 (106 g, 72%) as a white solid. M.p. 144-146° C. $[\alpha]^{20}_D$ +62.3 (c=1.0, EtOH).

Example 10

1-N-Benzyl-3-hydroxy-4-hydroxymethyl-pyrrolidine 7 by Reduction of ester 5

A solution of ester 5 (3.1 g, 12.4 mmol) in THF (100 mL) was cooled in an ice-water bath and then borane-dimethyl sulfide complex (6.0 mL, 58 mmol) was added via syringe.

The solution was allowed to warm to room temperature and then heated under reflux for 2 h. The reaction was cooled, quenched by portionwise additions of methanol and concentrated under reduced pressure on to silica gel (approx. 15 mL). The silica was applied to the top of a short silica gel column that was eluted with ethyl acetate. The eluant fractions containing the product were concentrated under reduced pressure and the residue stirred in TFA-water (1:1, 30 mL) overnight. Evaporation of solvent and passage through an ion exchange chromatography (Amberlite IRA-900, Cl⁻-form, eluted, with methanol-water, 1:1 v/v) gave an oil that was further chromatographed on silica gel (dichloromethane-methanol 6:1-4:1 as eluent) to give the title compound (1.50 g, 7.2 mmol, 58%).

Although the invention has been described by way of example, it should be appreciated that variations or modifications may be made without departing from the scope of the invention. Furthermore, when known equivalents exist to specific features, such equivalents are incorporated as if specifically referred to in the specification.

Industrial Applicability

The invention provides an improved process for preparing (3R,4R)-3-hydroxy-4-hydroxymethylpyrrolidine and its enantiomer (3R,4R)-3-hydroxy-4-hydroxymethylpyrrolidine, both of which are valuable intermediate compounds in the preparation of inhibitors of purine nucleoside phosphorylases. Such inhibitors are potential therapeutic agents for the treatment of a variety of diseases, particularly cancers.

The invention claimed is:

1. A process for preparing (3R,4R)-3-hydroxy-4-hydroxymethylpyrrolidine, the compound of formula (I), or (3S,4S)-3-hydroxy-4-hydroxymethylpyrrolidine, the compound of formula (Ia):

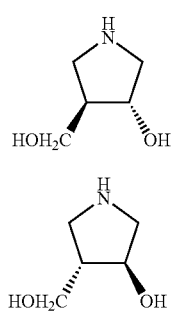

comprising the following steps:
step (a): enzyme-catalysed enantioselective hydrolysis of a racemic 3,4-trans-disubstituted pyrrolidinone compound of formula (II):

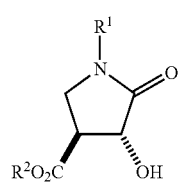

where $R^1$ is benzyl or benzhydryl, each of which may be optionally substituted by halogen, alkyl or alkoxy; and $R^2$ is aryl or straight or branched chain alkyl or aralkyl, any of which may be optionally substituted by halogen, alkyl or alkoxy;

to give either:
mixture (i): a 3,4-trans-disubstituted pyrrolidinone compound of formula (III) and unreacted pyrrolidinone compound of formula (IV):

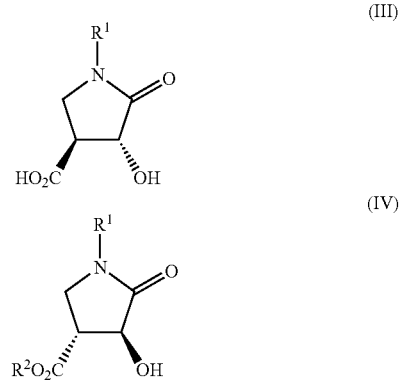

or
mixture (ii): a 3,4-trans-disubstituted pyrrolidinone compound of formula (IIIa), and unreacted pyrrolidinone compound of formula (IVa):

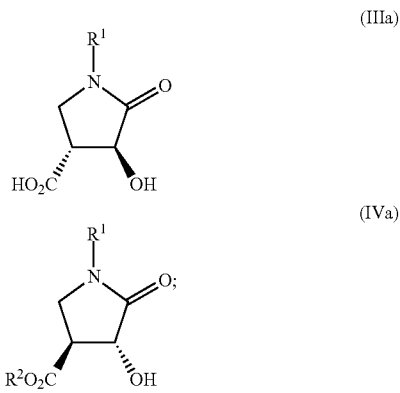

step (b): separation of the compound of formula (III) from the compound of formula (IV) in mixture (i), or separation of the compound of formula (IIIa) from the compound of formula (IVa) in mixture (ii); and step (c): transformation of the compound of formula (III) or the compound of formula (IVa) to the compound of formula (I), or transformation of the compound of formula (IV) or the compound of formula (IIIa) to the compound of formula (Ia).

2. A process as claimed in claim 1 where step (a) gives mixture (i) using an enzyme capable of producing an enantiomeric excess of compound (III) or mixture (ii) using an enzyme capable of producing an enantiomeric excess of compound (IIIa).

3. A process as claimed in claim 1 where the enzyme used in step (a) is a lipase or an esterase.

4. A process as claimed in claim 1 where step (c) is transformation of the compound of formula (III) to the compound of formula (I) or transformation of the compound of formula (IIIa) to the compound of formula (Ia).

5. A process as claimed in claim 4 where the transformation is effected by a process including the step of reduction of the compound of formula (III) or formula (IIIa) to give a 3,4-trans-disubstituted pyrrolidine compound of formula (V) or formula (Va):

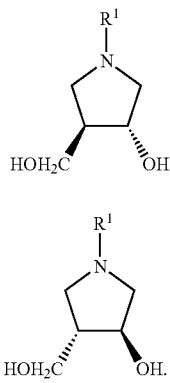

6. A process as claimed in claim 5 where the reduction is carried out using lithium aluminium hydride or borane.

7. A process as claimed in claim 5 where $R^1$ is benzyl and the compound of formula (V) or formula (Va) is recrystallised to improve its enantiomeric excess.

8. A process as claimed in claim 5 further including the step of replacement of the $R^1$ group of the compound of formula (V) or formula (Va) with hydrogen, to give the compound of formula (I) or formula (Ia).

9. A process as claimed in claim 8 where the replacement of the $R^1$ group with hydrogen is carried out by hydrogenolysis.

10. A process as claimed in claim 1 where the separation of the compound of formula (III) from the compound of formula (IV) in step (b) is carried out by extracting the compound of formula (IV) from an aqueous solution containing the compound of formula (IV) and a carboxylate salt form of the compound of formula (III) using a first water-immiscible solvent, then lowering the pH of the resulting mixture to convert the carboxylate salt form of the compound of formula (III) to the carboxylic acid form of the compound of formula (III), then extracting the resulting mixture again with a second water-immiscible solvent.

11. A process as claimed in claim 10 where the first water-immiscible solvent is dichloromethane or chloroform.

12. A process as claimed in claim 10 where the second water-immiscible solvent is ethyl acetate.

13. A process for preparing a 3,4-trans-disubstituted pyrrolidine compound of formula (VI) or formula (VIa):

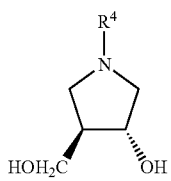

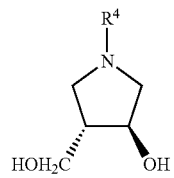

where $R^4$ is an N-protecting group; the process comprising preparing (3R,4R)-3-hydroxy-4-hydroxymethylpyrrolidine, the compound of formula (I), or (3S,4S)-3-hydroxy-4-hydroxymethylpyrrolidine, the compound of formula (Ia) by the process as claimed in claim 1; and converting the compound of formula (I) or formula (Ia) to the compound of formula (VI) or formula (VIa).

14. A process as claimed in claim 13 where $R^4$ is alkoxycarbonyl, aryloxycarbonyl or aralkoxycarbonyl.

15. A process as claimed in claim 14 where $R^4$ is tert-butoxycarbonyl, methoxycarbonyl or benzyloxycarbonyl.

16. A process as claimed in claim 13 where the compound of formula (VI) or (VIa) is recrystallised to improve its enantiomeric excess.

17. A process as claimed in claim 14 where the compound of formula (I) is converted to the compound of formula (VI) by treatment with an alkoxycarbonylating agent, an aryloxycarbonylating agent or an aralkoxycarbonylating agent, optionally in the presence of a base.

18. A process as claimed in claim 17 where the base is triethylamine or sodium hydroxide.

19. A process as claimed in claim 1 where the compound of formula (II) is prepared by a process including the step of reductive cleavage of the N—O bond of a 4,5-cis-disubstituted isoxazolidine compound of formula (VII), and in situ cyclisation to give the compound of formula (II):

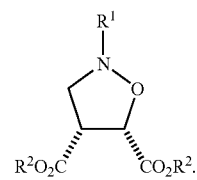

20. A process as claimed in claim 19 where the compound of formula (VII) is prepared by 1,3-cycloaddition of a nitrone of formula (VIII) and an alkene of formula (IX):

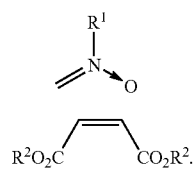

21. A process as claimed in claim 20 where the 1,3-cycloaddition is carried out by generating the nitrone of formula (VIII) and then allowing it to react in situ with the alkene of formula (IX).

22. A process as claimed in claim 19 where $R^1$ is benzyl.

23. A process as claimed in claim 20 where the nitrone of formula (VIII) is generated by reaction of N-benzylhydroxylamine and HCHO.

24. A process as claimed in claim 20 where $R^2$ is alkyl.

25. A process as claimed in claim 24 where $R^2$ is methyl or ethyl.

26. A process as claimed in claim 19 where the reductive cleavage and in situ cyclisation is carried out by hydrogenolysis or by using Zn in the presence of an acid.

27. A process for preparing a compound of formula (X) or (Xa):

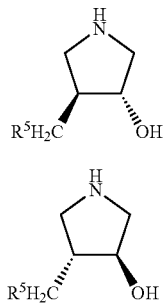

(X)

(Xa)

where $R^5$ is selected from H, OH and SH, or from alkyloxy, aralkyloxy, aryloxy, alkylthio, aralkylthio, and arylthio each of which may be substituted by halogen, branched or straight chain saturated or unsaturated alkyl, alkoxy, aralkyloxy or aryloxy; the process comprising
preparing (3R,4R)-3-hydroxy-4-hydroxymethylpyrrolidine, the compound of formula (I), or (3S,4S)-3-hydroxy-4-hydroxymethylpyrrolidine, the compound of formula (Ia) by the process as claimed in claim 1; and
converting the compound of formula (I) or formula (Ia) to the compound of formula (X) or formula (Xa).

28. A process for preparing a compound of formula (XII) or (XIIa):

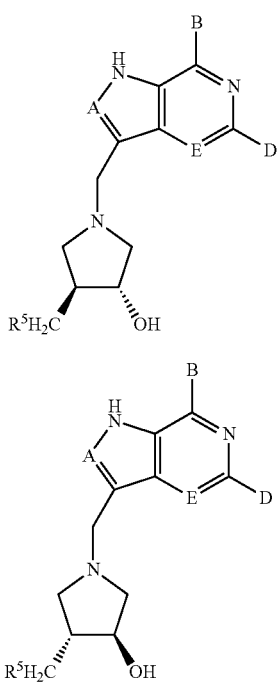

(XII)

(XIIa)

the process comprising
preparing a compound of formula (X) or formula (Xa) by the process of claim 27;
and
reacting the compound of formula (X) or (Xa) with a compound of formula (XI)

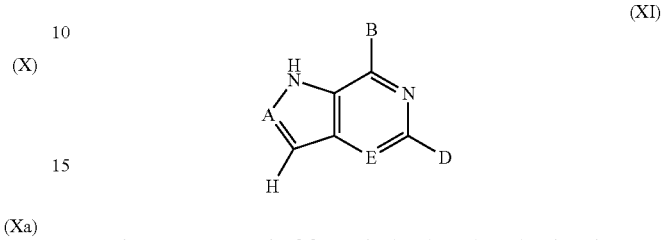

(XI)

to give a compound of formula (XII) or (XIIa); wherein
$R^5$ is selected from H, OH and SH, or from alkyloxy, aralkyloxy, aryloxy, alkylthio, aralkylthio, and arylthio each of which may be substituted by halogen, branched or straight chain saturated or unsaturated alkyl, alkoxy, aralkyloxy or aryloxy;
A is selected from N, CH and $CR^6$, where $R^6$ is selected from halogen, OH and $NH_2$, or $R^6$ is selected from alkyl, aralkyl and aryl, each of which may be substituted by halogen, branched or straight chain saturated or unsaturated alkyl, alkoxy, aralkyloxy or aryloxy, or $R^6$ is selected from $NHR^7$, $NR^7R^8$ and $SR^9$, where $R^7$, $R^8$ and $R^9$ are selected from alkyl, aralkyl and aryl each of which may be substituted by halogen, branched or straight chain saturated or unsaturated alkyl, alkoxy, aralkyloxy or aryloxy;
B is selected from OH, $NH_2$, $NHR^{10}$, SH, hydrogen and halogen, where $R^{10}$ is selected from alkyl, aralkyl and aryl each of which may be substituted by halogen, branched or straight chain saturated or unsaturated alkyl, alkoxy, aralkyloxy or aryloxy;
D is selected from OH, $NH_2$, $NHR^{11}$, hydrogen, halogen and $SCH_3$, where $R^{11}$ is selected from alkyl, aralkyl and aryl each of which may be substituted by halogen, branched or straight chain saturated or unsaturated alkyl, alkoxy, aralkyloxy or aryloxy; and;
E is selected from N and CH.

29. A process as claimed in claim 28 where the reaction is carried out using formaldehyde or a formaldehyde equivalent.

30. A process as claimed in claim 28 where the compound of formula (XI) is converted into a compound of formula (XIII) and then reacting the compound of formula (X) or (Xa) with a compound of formula (XIII) to give a compound of formula (XII) or (XIIa):

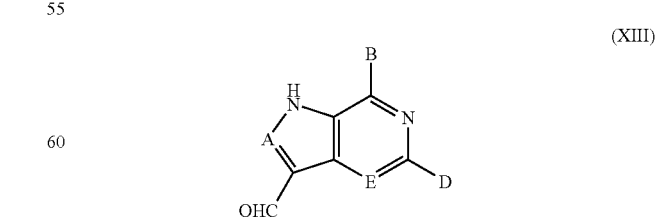

(XIII)

where A, B, D and E each of which, and the NH in the 5-membered ring, may be protected with suitable protecting groups.

31. A process for preparing a compound of formula (X) or (Xa):

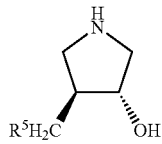
(X)

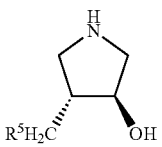
(Xa)

where $R^5$ is selected from H, OH and SH, or from alkyloxy, aralkyloxy, aryloxy, alkylthio, aralkylthio, and arylthio each of which may be substituted by halogen, branched or straight chain saturated or unsaturated alkyl, alkoxy, aralkyloxy or aryloxy; the process comprising preparing (3R,4R)-3-hydroxy-4-hydroxymethylpyrrolidine, the compound of formula (I), or (3S,4S)-3-hydroxy-4-hydroxymethylpyrrolidine, the compound of formula (Ia) by the process as claimed in claim 21; and converting the compound of formula (I) or formula (Ia) to the compound of formula (X) or formula (Xa).

32. A process for preparing a compound of formula (XII) or (XIIa);

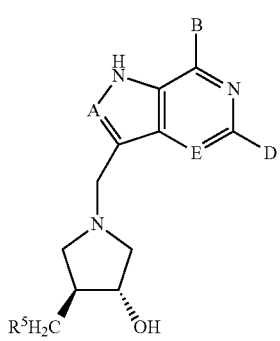
(XII)

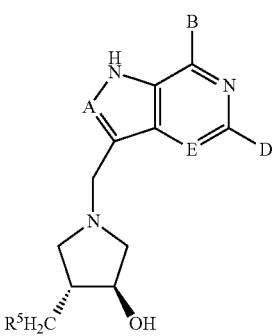
(XIIa)

the process comprising preparing a compound of formula (X) or formula (Xa) by the process of claim 31;
and
reacting the compound of formula (X) or (Xa) with a compound of formula (XI)

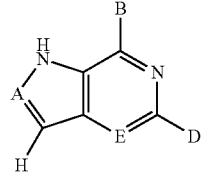
(XI)

to give a compound of formula (XII) or (XIIa); wherein $R^5$ is selected from H, OH and SH, or from alkyloxy, aralkyloxy, aryloxy, alkylthio, aralkylthio, and arylthio each of which may be substituted by halogen, branched or straight chain saturated or unsaturated alkyl, alkoxy, aralkyloxy or aryloxy;

A is selected from N, CH and $CR^6$, where $R^6$ is selected from halogen, OH and $NH_2$, or $R^6$ is selected from alkyl, aralkyl and aryl, each of which may be substituted by halogen, branched or straight chain saturated or unsaturated alkyl, alkoxy, aralkyloxy or aryloxy, or $R^6$ is selected from $NHR^7$, $NR^7,R^8$ and $SR^9$, where $R^7$, $R^8$ and $R^9$ are selected from alkyl, aralkyl and aryl each of which may be substituted by halogen, branched or straight chain saturated or unsaturated alkyl, alkoxy, aralkyloxy or aryloxy;

B is selected from OH, $NH_2$, $NHR^{10}$, SH, hydrogen and halogen, where $R^{10}$ is selected from alkyl, aralkyl and aryl each of which may be substituted by halogen, branched or straight chain saturated or unsaturated alkyl, alkoxy, aralkyloxy or aryloxy;

D is selected from OH, $NH_2$, $NHR^{11}$, hydrogen, halogen and $SCH_3$, where $R^{11}$ is selected from alkyl, aralkyl and aryl each of which may be substituted by halogen, branched or straight chain saturated or unsaturated alkyl, alkoxy, aralkyloxy or aryloxy; and;

E is selected from N and CH.

33. A process for preparing (3R,4R)-3-hydroxy-4-hydroxymethylpyrrolidine, the compound of formula (I), or (3S,4S)-3-hydroxy-4-hydroxymethylpyrrolidine, the compound of formula (Ia):

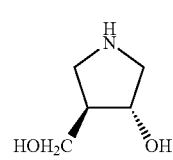
(I)

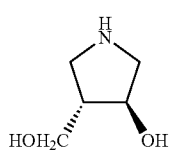
(Ia)

including the steps of:

(i) 1,3-cycloaddition of a nitrone of formula (2) and an alkene of formula (3) to give a 4,5-cis-disubstituted isoxazolidine compound of formula (4):

(2)
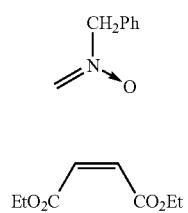

(3)
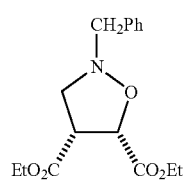

(4)
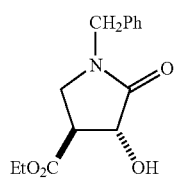

(ii) reductive cleavage of the N—O bond of the 4,5-cis-disubstituted isoxazolidine compound of formula (4) and in situ cyclisation to give a 3,4-trans-disubstituted pyrrolidinone compound of formula (5):

(5)
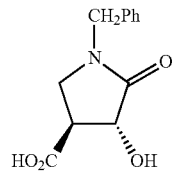

(iii) enzyme-catalysed enantioselective hydrolysis of the compound of formula (5) to give a mixture of a compound of formula (6), and unreacted compound of formula (5), or a mixture of a compound of formula (6a), and unreacted compound of formula (5a):

(6)
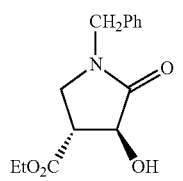

(5)

(6a)
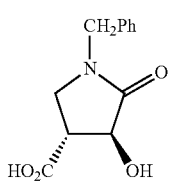

(5a)
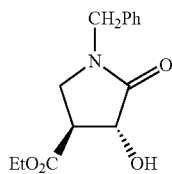

(iv) separation of the compound of formula (6) from the compound of formula (5), or separation of compound of formula (6a) from the compound of formula (5a);

(v) reduction of the compound of formula (6) or (5a) to give a compound of formula (7), or reduction of the compound of formula (6a) or (5) to give a compound of formula (7a)

(7)
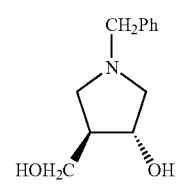

(7a)
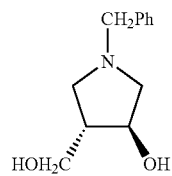

(vi) replacement of the CH$_2$Ph group with hydrogen in the compound of formula (7) to give the compound of formula (I), or replacement of the CH$_2$Ph group with hydrogen in the compound of formula (7a) to give the compound of formula (Ia).

34. A process as claimed in claim 33 further including the step of:

(vii) conversion of the compound of formula (I) to a compound of formula (8), or conversion of the compound of formula (Ia) to a compound of formula (8a):

(8)
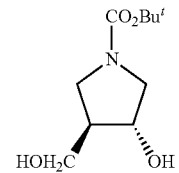

(8a)
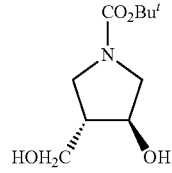

by treatment of the compound of formula (I), or the compound of formula (Ia) with di-tert-butyldicarbonate or di-tert-butyldicarbonate.

35. A process as claimed in claim 34 where the compound of formula (I), or the compound of formula (Ia), is not isolated, and the conversion of the compound of formula (I) to the compound of formula (8), or the compound of formula (Ia) to the compound of formula (8a), in step (vii) is effected in situ.

36. A compound of formula (III):

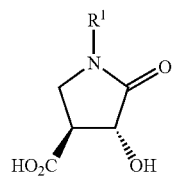

(III)

where $R^1$ is benzyl or benzhydryl, each of which may be optionally substituted by halogen, alkyl or alkoxy.

37. A compound of formula (IV):

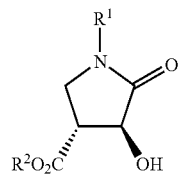

(IV)

where $R^1$ is benzyl or benzhydryl, each of which may be optionally substituted by halogen, alkyl or alkoxy; and $R^2$ is aryl or straight or branched chain alkyl or aralkyl, any of which may be optionally substituted by halogen, alkyl or alkoxy.

* * * * *